US008768516B2

(12) United States Patent  
Diolaiti et al.

(10) Patent No.: US 8,768,516 B2  
(45) Date of Patent: Jul. 1, 2014

(54) CONTROL OF MEDICAL ROBOTIC SYSTEM MANIPULATOR ABOUT KINEMATIC SINGULARITIES

(75) Inventors: Nicola Diolaiti, Palo Alto, CA (US); Giuseppe M. Prisco, Mountain View, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 898 days.

(21) Appl. No.: 12/494,695

(22) Filed: Jun. 30, 2009

(65) Prior Publication Data  
US 2010/0332033 A1 Dec. 30, 2010

(51) Int. Cl.  
*G05B 15/00* (2006.01)  
*G05B 19/00* (2006.01)

(52) U.S. Cl.  
USPC ............ 700/262; 700/245; 700/259; 700/263

(58) Field of Classification Search  
USPC ................. 700/245, 259, 262, 263; 901/8, 11  
See application file for complete search history.

(56) References Cited

U.S. PATENT DOCUMENTS

| | | | | |
|---|---|---|---|---|
| 4,716,350 A | * | 12/1987 | Huang et al. | ............... 318/568.2 |
| 4,763,276 A | | 8/1988 | Perreirra et al. | |
| 5,036,724 A | | 8/1991 | Rosheim | |
| 5,038,089 A | | 8/1991 | Szakaly | |
| 5,336,982 A | * | 8/1994 | Backes | ................... 318/568.22 |
| 5,430,643 A | | 7/1995 | Seraji | |
| 5,454,533 A | * | 10/1995 | Grant et al. | ............... 244/134 R |
| 5,590,034 A | * | 12/1996 | Snell | ............................. 700/61 |
| 5,697,285 A | * | 12/1997 | Nappi et al. | ................... 91/519 |
| 5,710,870 A | | 1/1998 | Ohm et al. | |

(Continued)

FOREIGN PATENT DOCUMENTS

EP 1433431 A1 1/2006

OTHER PUBLICATIONS

Albu-Schäffer, Alin and Gerd Hirzinger, "Cartesian Impedance Control Techniques for Torque Controlled Light-Weight Robots," IEEE International Conference on Robotics and Automation, IEEE, 2002, vol. 1, pp. 657-663.

(Continued)

*Primary Examiner* — Khoi Tran  
*Assistant Examiner* — Jorge Peche

(57) ABSTRACT

A medical robotic system includes an entry guide with articulatable instruments extending out of its distal end, an entry guide manipulator providing controllable four degrees-of-freedom movement of the entry guide relative to a remote center, and a controller configured to manage operation of the entry guide manipulator in response to operator manipulation of one or more input devices. As the entry guide manipulator approaches a yaw/roll singularity, the controller modifies its operation to allow continued movement of the entry guide manipulator without commanding excessive joint velocities while maintaining proper orientation of the entry guide.

6 Claims, 10 Drawing Sheets

(56) References Cited

U.S. PATENT DOCUMENTS

| | | | |
|---|---|---|---|
| 5,737,500 A | | 4/1998 | Seraji et al. |
| 5,784,542 A | | 7/1998 | Ohm et al. |
| 5,828,813 A | | 10/1998 | Ohm |
| 6,047,610 A | | 4/2000 | Stocco et al. |
| 6,233,504 B1 | | 5/2001 | Das et al. |
| 6,278,906 B1 * | | 8/2001 | Piepmeier et al. ............ 700/250 |
| 6,385,509 B2 | | 5/2002 | Das et al. |
| 6,456,901 B1 * | | 9/2002 | Xi et al. ........................ 700/245 |
| 6,491,491 B1 * | | 12/2002 | Tsuneda et al. ........... 414/744.5 |
| 6,671,581 B2 | | 12/2003 | Niemeyer et al. |
| 6,676,684 B1 | | 1/2004 | Morley et al. |
| 6,684,129 B2 * | | 1/2004 | Salisbury et al. ............ 700/245 |
| 6,685,698 B2 | | 2/2004 | Morley et al. |
| 6,714,839 B2 * | | 3/2004 | Salisbury et al. ............ 700/245 |
| 6,723,106 B1 | | 4/2004 | Charles et al. |
| 6,746,443 B1 | | 6/2004 | Morley et al. |
| 6,817,974 B2 | | 11/2004 | Cooper et al. |
| 6,902,560 B1 | | 6/2005 | Morley et al. |
| 7,021,173 B2 | | 4/2006 | Stoianovici et al. |
| 7,056,191 B2 * | | 6/2006 | Takatsuji et al. ................ 451/28 |
| 7,086,307 B2 * | | 8/2006 | Gosselin et al. .......... 74/490.06 |
| 7,320,700 B2 | | 1/2008 | Cooper et al. |
| 7,398,707 B2 | | 7/2008 | Morley et al. |
| 7,453,227 B2 | | 11/2008 | Prisco et al. |
| 7,736,356 B2 | | 6/2010 | Cooper et al. |
| 7,741,802 B2 | | 6/2010 | Prisco et al. |
| 7,862,580 B2 | | 1/2011 | Cooper et al. |
| 7,865,269 B2 | | 1/2011 | Prisco et al. |
| 7,899,578 B2 | | 3/2011 | Prisco et al. |
| 7,930,065 B2 * | | 4/2011 | Larkin et al. ................. 700/245 |
| 2001/0020200 A1 | | 9/2001 | Das et al. |
| 2001/0041129 A1 * | | 11/2001 | Tsuneda et al. ........... 414/744.1 |
| 2002/0048505 A1 * | | 4/2002 | Tsuneda et al. ........... 414/744.1 |
| 2002/0120363 A1 * | | 8/2002 | Salisbury et al. ............ 700/254 |
| 2003/0023346 A1 * | | 1/2003 | Salisbury et al. ............ 700/245 |
| 2003/0146720 A1 * | | 8/2003 | Riwan et al. ...................... 318/1 |
| 2003/0151379 A1 * | | 8/2003 | Gosselin et al. .................. 318/1 |
| 2004/0035243 A1 | | 2/2004 | Duval |
| 2004/0213915 A1 * | | 10/2004 | Andersen ................... 427/421.1 |
| 2005/0090809 A1 | | 4/2005 | Cooper et al. |
| 2005/0096694 A1 | | 5/2005 | Lee |
| 2005/0129495 A1 * | | 6/2005 | Brogardh ...................... 414/680 |
| 2006/0015214 A1 * | | 1/2006 | Sugawara et al. ............ 700/245 |
| 2006/0060021 A1 * | | 3/2006 | Riwan et al. .............. 74/490.04 |
| 2006/0199999 A1 | | 9/2006 | Ikeda et al. |
| 2006/0253109 A1 * | | 11/2006 | Chu ................................. 606/1 |
| 2006/0293790 A1 * | | 12/2006 | Gienger ........................ 700/245 |
| 2007/0106306 A1 * | | 5/2007 | Bodduluri et al. ............ 606/133 |
| 2007/0106307 A1 * | | 5/2007 | Bodduluri et al. ............ 606/133 |
| 2007/0138992 A1 | | 6/2007 | Prisco et al. |
| 2007/0142825 A1 | | 6/2007 | Prisco et al. |
| 2007/0142968 A1 | | 6/2007 | Prisco et al. |
| 2007/0197939 A1 * | | 8/2007 | Wallace et al. ............... 600/587 |
| 2007/0233044 A1 * | | 10/2007 | Wallace et al. ............... 604/528 |
| 2008/0046122 A1 | | 2/2008 | Manzo et al. |
| 2008/0103492 A1 | | 5/2008 | Morley et al. |
| 2008/0203230 A1 * | | 8/2008 | Ogo et al. ...................... 244/165 |
| 2009/0088775 A1 * | | 4/2009 | Swarup et al. ................ 606/130 |
| 2009/0192519 A1 * | | 7/2009 | Omori ........................... 606/130 |
| 2010/0206120 A1 * | | 8/2010 | Kinoshita et al. .......... 74/490.06 |
| 2010/0228284 A1 | | 9/2010 | Cooper et al. |
| 2010/0228396 A1 * | | 9/2010 | Pechev .......................... 700/263 |
| 2011/0046925 A1 * | | 2/2011 | Bidard et al. ..................... 703/2 |
| 2011/0118755 A1 | | 5/2011 | Cooper et al. |
| 2011/0125166 A1 | | 5/2011 | Cooper et al. |
| 2011/0160904 A1 | | 6/2011 | Prisco et al. |
| 2011/0166706 A1 | | 7/2011 | Prisco et al. |

OTHER PUBLICATIONS

Baumann, Roger, "Haptic Interface for Virtual Reality Based Laparoscopic Surgery Training Environment," Theses No. 1734 Ecole Pholytechnique Federale de Lausanne, 1997, 104 Total Pages.

Bejczy, Antal K. et al., "Controlling Remote Manipulators through Kinesthetic Coupling," Computers in Mechanical Engineering, 1983, pp. 48-60, vol. 1-Issue 1.

Charles, Steve et al., "Dexterity-enhanced Telerobotic Microsurgery," 1997, pp. 5-10, IEEE.

Kelly, Alonzo, "Linearized Error Propagation in Odometry," The International Journal of Robotics Research, 2004, pp. 179-218, vol. 23—Issue 2, SAGE Publications.

Lum, Mitchell Jay Hiroshi, "Kinematic Optimization of a 2-DOF Spherical Mechanism for a Minimally Invasive Surgical Robot," Proc. IEEE Conf. Robotics and Automation, 2004, 69 Pages, IEEE.

Mair, Gordon M., Industrial Robotics, Prentice Hall, 1988, pp. 41-43, 49-50, 54, 203-209.

Mcaffee, Douglas A. et al., "Teleoperator Subsystem Telerobot. Demonstrator: Force Reflecting Hand Controller Equipment Manual," 1988, 131 Pages Total.

Moyer, Thomas H., "The design for an integrated hand and wrist mechanism," Masters Thesis, Feb. 1992, 52 pages, Massachusetts Institute of Technology.

Nakamura, Yoshihiko et al., "Unified Recursive Formulation of Kinematics and Dynamics of Robot Manipulators," Proc. Japan-USA Symposium on Flexible Automation, 1986, pp. 53-60.

Niemeyer, Gunter, "Mathematical System Description," 2000, 25 pages.

Rosheim, Mark E., Chapter 5: "Pitch-Yaw-Roll Wrists," Robot Wrist Actuators, Wiley & Sons, New York, 1989, pp. 95-206.

Rosheim, Mark E., "Robot Evolution: Development of Anthrobotics," Pub. John Wiley & Sons, Inc., New York, 1994, Chapter 2, pp. 37-156.

Rosheim, Mark E., "Robot Wrist Actuators, 1995," pp. 95-206, a Wiley-Interscience Publication.

Roy, Jaydeep, "Advances in the design, analysis and control of force controlled robots," Master's Thesis, Mechanical Engineering, Johns Hopkins University, Baltimore, 2001, 210 Pages.

Schenker Paul S. et al., "Development of a New High Dexterity Manipulator for Robot Assisted Microsurgery," Proceedings of SPIE, The Intl.Society for Optical Engineering, 1994, pp. 191-198, vol. 2351.

Schenker, Paul S. et al., "Development of a Telemanipulator for Dexterity Enhanced Microsurgery," 2nd Annual International Symposium on Medical Robotics and Computer Assisted Surgery, Nov. 4-7, Baltimore, Maryland, 1995, pp. 81-88.

Tourassis, Vassilios D. et al., "Identification and Analysis of Robot Manipulator Singularities," The International Journal of Robotics Research, 1992, pp. 248-259, vol. 11—Issue 3, SAGE Publications.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

Wampler, Charles W. et al., "Wrist singularities: Theory and practice," The Robotics Review 2, 1992, pp. 173-189, MIT Press.

Zhao, Wenyi et al., "Face Recognition: A Literature Survey," ACM Computing Surveys, Dec. 2003, vol. 35, No. 4, pp. 399-459.

* cited by examiner

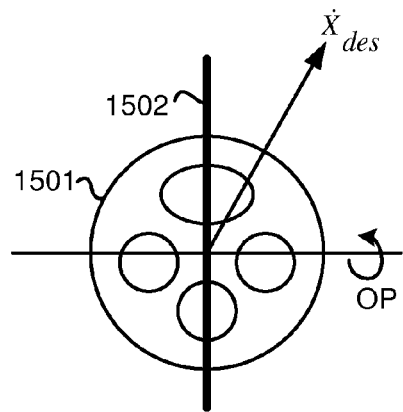
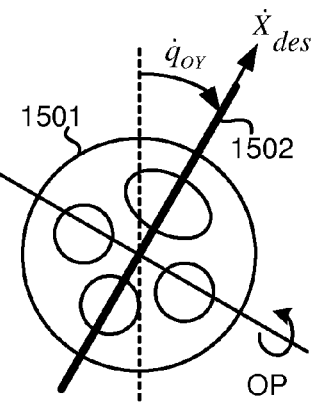
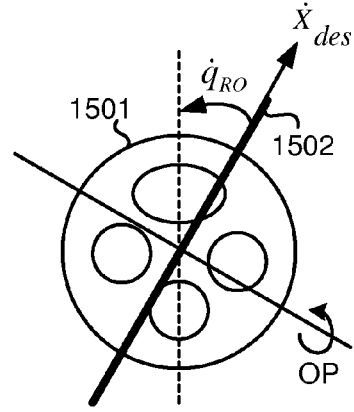
fig.15　　　　fig.16　　　　fig.17
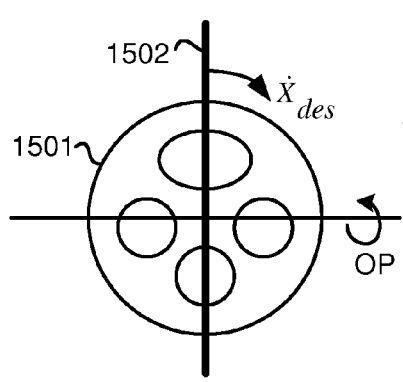
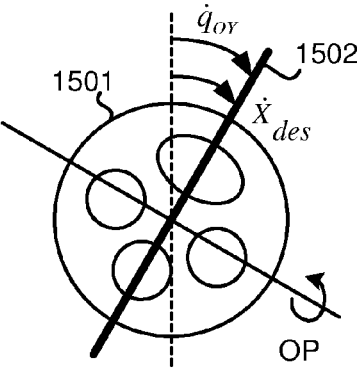
fig.18　　　　fig.19

CONTROL OF MEDICAL ROBOTIC SYSTEM MANIPULATOR ABOUT KINEMATIC SINGULARITIES

FIELD OF THE INVENTION

The present invention generally relates to medical robotic systems and in particular, to the control of a medical robotic system manipulator about kinematic singularities.

BACKGROUND OF THE INVENTION

Medical robotic systems such as teleoperative systems used in performing minimally invasive surgical procedures offer many benefits over traditional open surgery techniques, including less pain, shorter hospital stays, quicker return to normal activities, minimal scarring, reduced recovery time, and less injury to tissue. Consequently, demand for such medical robotic systems is strong and growing.

One example of such a medical robotic system is the da Vinci® Surgical System from Intuitive Surgical, Inc., of Sunnyvale, Calif., which is a minimally invasive robotic surgical system. The da Vinci® Surgical System has a number of robotic arms that move attached medical devices, such as an image capturing device and Intuitive Surgical's proprietary EndoWrist® articulating surgical instruments, in response to movement of input devices by a surgeon viewing images captured by the image capturing device of a surgical site. Each of the medical devices is inserted through its own minimally invasive incision into the patient and positioned to perform a medical procedure at the surgical site. The incisions are placed about the patient's body so that the surgical instruments may be used to cooperatively perform the medical procedure and the image capturing device may view it without their robotic arms colliding during the procedure.

To perform certain medical procedures, it may be advantageous to use a single entry aperture, such as a minimally invasive incision or a natural body orifice, to enter a patient to perform a medical procedure. For example, an entry guide may first be inserted, positioned, and held in place in the entry aperture. Instruments such as an articulatable camera and a plurality of articulatable surgical tools, which are used to perform the medical procedure, may then be inserted into a proximal end of the entry guide so as to extend out of its distal end. Thus, the entry guide provides a single entry aperture for multiple instruments while keeping the instruments bundled together as it guides them toward the work site.

To properly guide the instruments to and maneuver them about a work site within a patient, an entry guide manipulator commandable through operator interaction with one or more input devices is desirable to move the entry guide through and about a pivot point at the entry aperture. In doing so, however, it is important to maintain good control of the entry guide manipulator when encountering singularities in its operation. In particular, it is desirable to avoid control problems encountered when axes for two rotational degrees of freedom of an entry guide manipulator coincide during its operation. Conventional systems employ either a control system that avoids operating at a singularity using a so-called "no-fly zone", which limits the workspace of the manipulator, or redundant degrees-of-freedom, which allow the manipulator to reach the desired tip position and orientation without approaching the singularity.

OBJECTS AND SUMMARY OF THE INVENTION

Accordingly, one object of one or more aspects of the present invention is a medical robotic system and method implemented therein for positioning and/or orienting a medical device using a manipulator without losing good control of the manipulator when encountering a singularity in its operation.

Another object of one or more aspects of the present invention is a medical robotic system and method implemented therein for positioning and/or orienting a medical device using a manipulator without avoiding operation at a singularity of the manipulator.

Another object of one or more aspects of the present invention is a medical robotic system and method implemented therein that retains intuitive tele-operation of a non-redundant manipulator while it operates around and at a singularity of the manipulator.

Another object of one or more aspects of the present invention is a medical robotic system and method incorporated therein for positioning and/or orienting a medical device having a camera extending out of its distal end without unintentionally changing the orientation of an image captured by the camera while operating at or near a singularity of a manipulator used for such positioning and/or orienting.

These and additional objects are accomplished by the various aspects of the present invention, wherein briefly stated, one aspect is a medical robotic system comprising: a medical device, a manipulator, and a controller. The manipulator is capable of manipulating the medical device in at least first, second and third rotational degrees of freedom in which the medical device is respectively rotatable about first, second and third axes at a pivot point. The first axis is fixed in space, and the second and third axes are fixed relative to the medical device and orthogonal to each other so as to move in space as the medical device moves. The controller is configured to command the manipulator to manipulate the medical device to the commanded state while resolving any control ambiguity caused by the first and the third axes coinciding.

Another aspect is a method for controlling a manipulator for manipulating a medical device in at least first, second and third rotational degrees of freedom in which the medical device is respectively rotatable about first, second and third axes at a pivot point, the first axis fixed in space, and the second and third axes fixed relative to the medical device and orthogonal to each other so as to move in space as the medical device moves. The method comprising: commanding the manipulator to manipulate the medical device to a commanded state while resolving any control ambiguity caused by the first and third axes coinciding.

Additional objects, features and advantages of the various aspects of the present invention will become apparent from the following description of its preferred embodiment, which description should be taken in conjunction with the accompanying drawings.

BRIEF DESCRIPTION OF THE DRAWINGS

FIGS. 15-17 illustrate sequential views of an entry guide tip as it changes its allowed direction and compensates for unintended changes to its orientation at a yaw/roll singularity, utilizing aspects of the present invention.

FIGS. 18-19 illustrate sequential views of an entry guide tip during a roll rotation of the tip about its axis at a yaw/roll singularity, utilizing aspects of the present invention.

DETAILED DESCRIPTION OF THE PREFERRED EMBODIMENT

Figure 1:
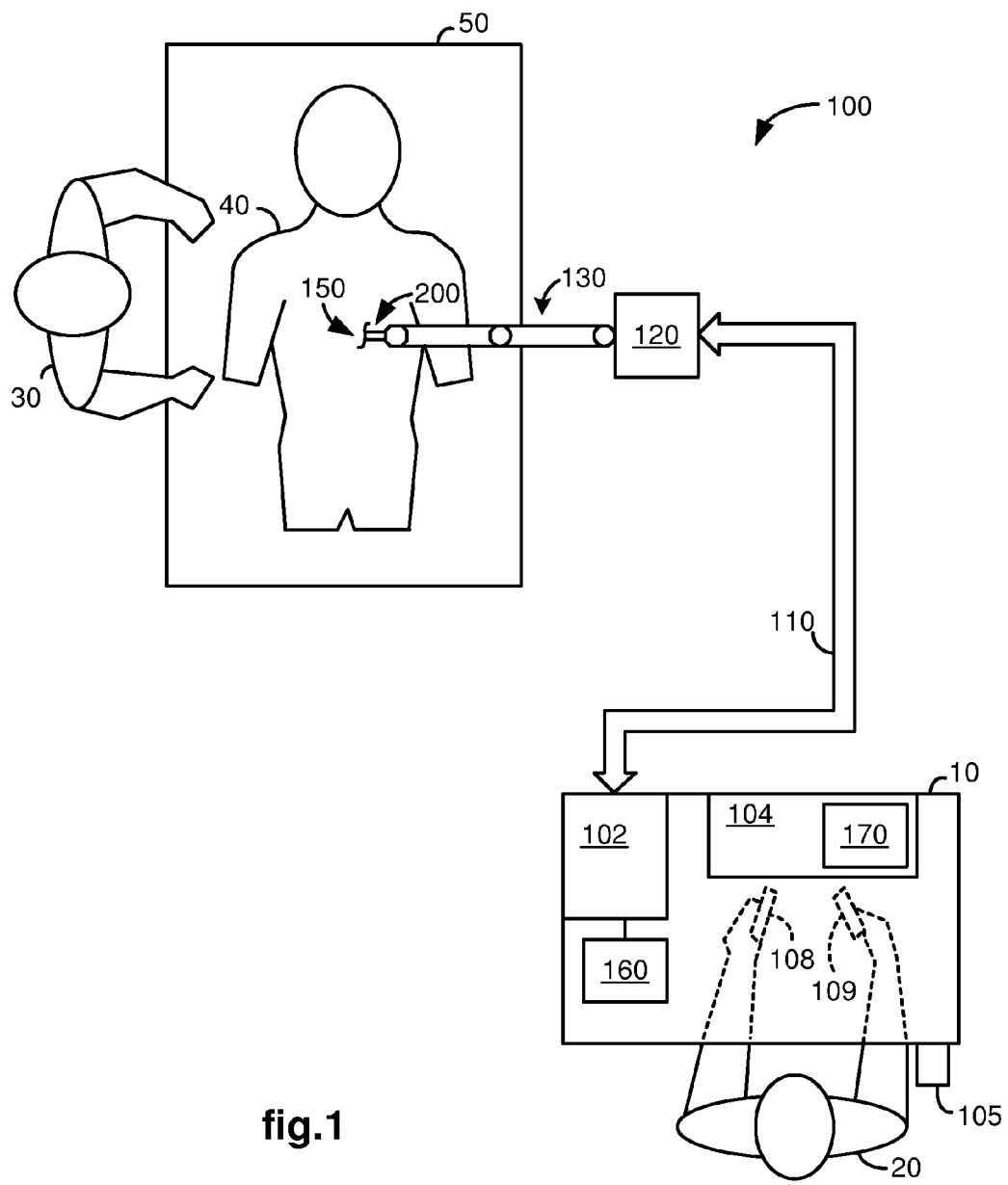
FIG. 1 illustrates a top view of an operating room employing a medical robotic system utilizing aspects of the present invention.

FIG. 1 illustrates, as an example, a top view of an operating room in which a medical robotic system 100 is being utilized by a Surgeon 20 for performing a medical procedure on a Patient 40 who is lying face up on an operating table 50. One or more Assistants 30 may be positioned near the Patient 40 to assist in the procedure while the Surgeon 20 performs the procedure teleoperatively by manipulating input devices 108, 109 on a surgeon console 10.

In the present example, an entry guide (EG) 200 is inserted through a single entry aperture 150 into the Patient 40. Although the entry aperture 150 is a minimally invasive incision in the present example, in the performance of other medical procedures, it may instead be a natural body orifice. The entry guide 200 is held and manipulated by a robotic arm assembly 130.

Figure 5:
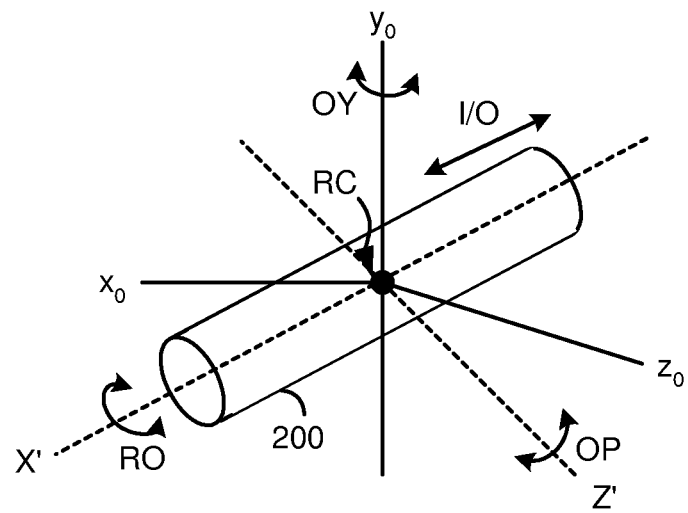
FIG. 5 illustrates a perspective view of an entry guide along with four degrees-of-freedom movement as used in a medical robotic system utilizing aspects of the present invention.
Figure 7:
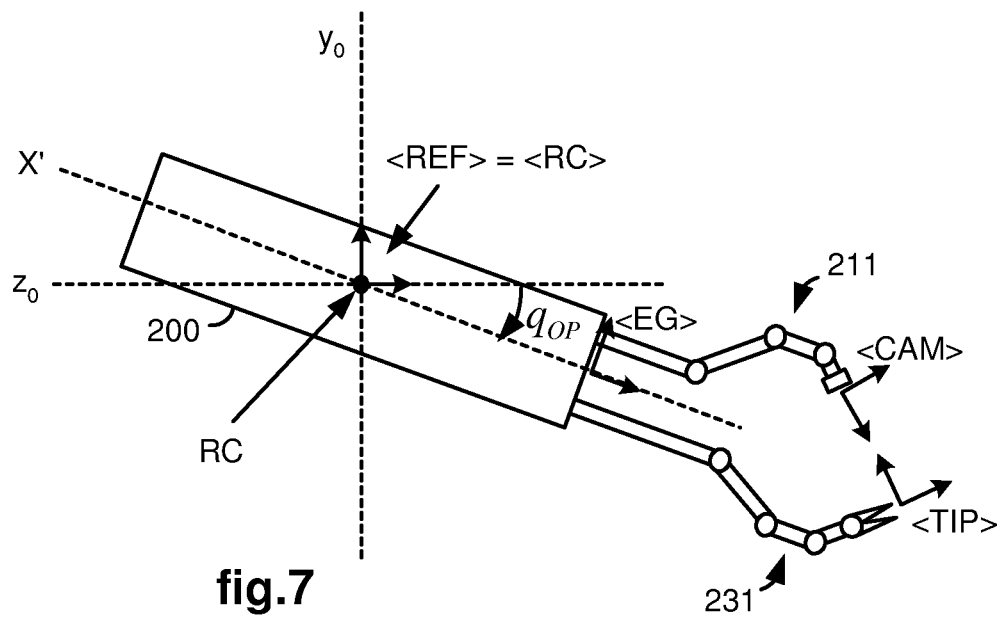
FIG. 7 illustrates a side view of an entry guide with various reference frames and a pitch angle indicated thereon as uses in a medical robotic system utilizing aspects of the present invention.

As with other parts of the medical robotic system 100, the illustration of the robotic arm assembly 130 is simplified in FIG. 1. In one example of the medical robotic system 100, the robotic arm assembly 130 includes a setup arm and an entry guide manipulator. The setup arm is used to position the entry guide 200 at the entry aperture 150 so that it properly enters the entry aperture 150. The entry guide manipulator is then used to robotically insert and retract the entry guide 200 into and out of the entry aperture 150. It may also be used to robotically pivot the entry guide 200 in pitch, roll and yaw about a pivot point located at the entry aperture 150. An example of such an entry guide manipulator is the entry guide manipulator 202 of FIG. 2 and an example of the four degrees-of-freedom movement that it manipulates the entry guide 200 with is shown in FIG. 5.

The console 10 includes a 3-D monitor 104 for displaying a 3-D image of a surgical site to the Surgeon, left and right hand-manipulatable input devices 108, 109, and a processor (also referred to herein as a "controller") 102. The input devices 108, 109 may include any one or more of a variety of input devices such as joysticks, gloves, trigger-guns, hand-operated controllers, or the like. Other input devices that are provided to allow the Surgeon to interact with the medical robotic system 100 include a foot pedal 105, a conventional voice recognition system 160 and a Graphical User Interface (GUI) 170.

The console 10 is usually located in the same room as the Patient so that the Surgeon may directly monitor the procedure, is physically available if necessary, and is able to speak to the Assistant(s) directly rather than over the telephone or other communication medium. However, it will be understood that the Surgeon can also be located in a different room, a completely different building, or other remote location from the Patient allowing for remote surgical procedures.

Figure 3:
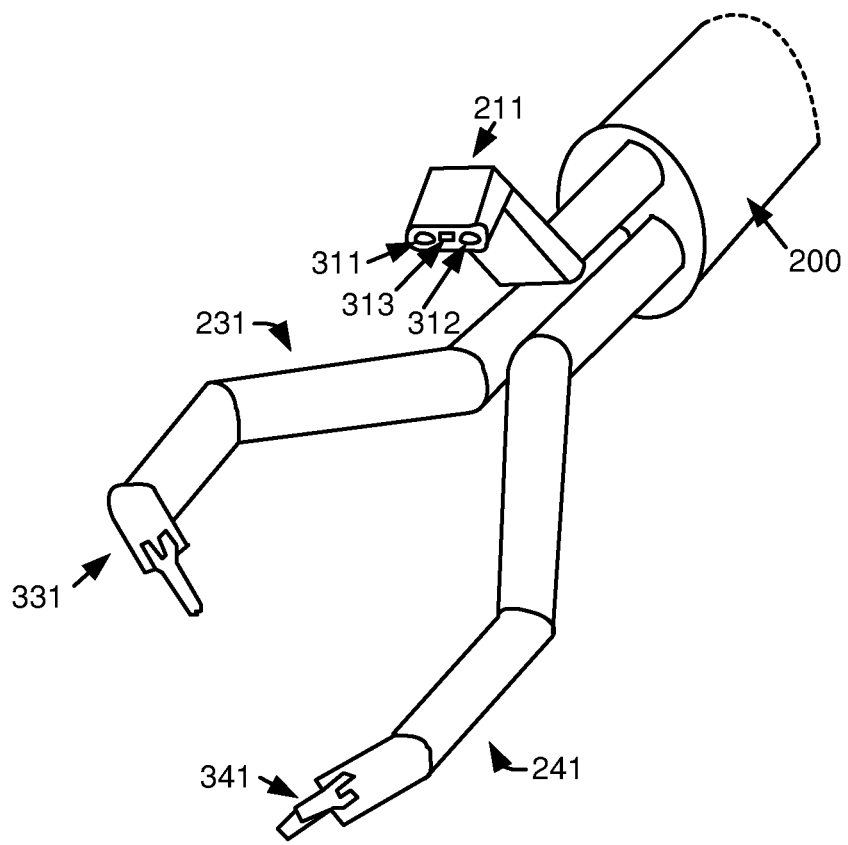
FIG. 3 illustrates a perspective view of a distal end of an entry guide with a plurality of articulatable instruments extending out of it in a medical robotic system utilizing aspects of the present invention.
Figure 4:
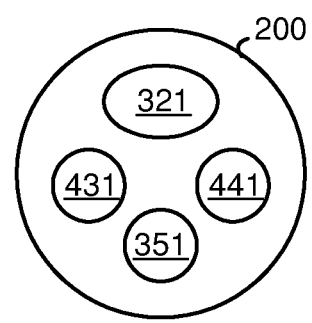
FIG. 4 illustrates a cross-sectional view of an entry guide as used in a medical robotic system utilizing aspects of the present invention.

As shown in FIG. 3, the entry guide 200 has articulatable instruments such as articulatable surgical tools 231, 241 and an articulatable stereo camera 211 extending out of its distal end. The camera has a stereo pair of image capturing devices 311, 312 and a fiber optic cable 313 (coupled at its proximal end to a light source) housed in its tip. The surgical tools 231, 241 have end effectors 331, 341. Although only two tools 231, 241 are shown, the entry guide 200 may guide additional tools as required for performing a medical procedure at a work site in the Patient. For example, as shown in FIG. 4, a passage 351 is available for extending another articulatable surgical tool through the entry guide 200 and out through its distal end. Each of the surgical tools 231, 241 is associated with one of the input devices 108, 109 in a tool following mode. The Surgeon performs a medical procedure by manipulating the input devices 108, 109 so that the controller 102 causes corresponding movement of their respectively associated surgical tools 231, 241 while the Surgeon views the work site in 3-D on the console monitor 104 as images of the work site are being captured by the articulatable camera 211.

Preferably, input devices 108, 109 will be provided with at least the same degrees of freedom as their associated tools 231, 241 to provide the Surgeon with telepresence, or the perception that the input devices 108, 109 are integral with the tools 231, 241 so that the Surgeon has a strong sense of directly controlling the tools 231, 241. To this end, the monitor 104 is also positioned near the Surgeon's hands so that it will display a projected image that is oriented so that the Surgeon feels that he or she is actually looking directly down onto the work site and images of the tools 231, 241 appear to be located substantially where the Surgeon's hands are located.

In addition, the real-time image on the monitor 104 is preferably projected into a perspective image such that the Surgeon can manipulate the end effectors 331, 341 of the tools 231, 241 through their corresponding input devices 108, 109 as if viewing the work site in substantially true presence.

By true presence, it is meant that the presentation of an image is a true perspective image simulating the viewpoint of an operator that is physically manipulating the end effectors 331, 341. Thus, the processor 102 transforms the coordinates of the end effectors 331, 341 to a perceived position so that the perspective image being shown on the monitor 104 is the image that the Surgeon would see if the Surgeon was located directly behind the end effectors 331, 341.

The processor 102 performs various functions in the system 100. One important function that it performs is to translate and transfer the mechanical motion of input devices 108, 109 through control signals over bus 110 so that the Surgeon can effectively manipulate devices, such as the tools 231, 241, camera 211, and entry guide 200, that are selectively associated with the input devices 108, 109 at the time. Another function is to perform various methods and implement various controllers described herein.

Although described as a processor, it is to be appreciated that the processor 102 may be implemented in practice by any combination of hardware, software and firmware. Also, its functions as described herein may be performed by one unit or divided up among different components, each of which may be implemented in turn by any combination of hardware, software and firmware. Further, although being shown as part of or being physically adjacent to the console 10, the processor 102 may also comprise a number of subunits distributed throughout the system.

For additional details on the construction and operation of various aspects of a medical robotic system such as described herein, see, e.g., U.S. Pat. No. 6,493,608 "Aspects of a Control System of a Minimally Invasive Surgical Apparatus," and U.S. Pat. No. 6,671,581 "Camera Referenced Control in a Minimally Invasive Surgical Apparatus," which are incorporated herein by reference.

Figure 2:
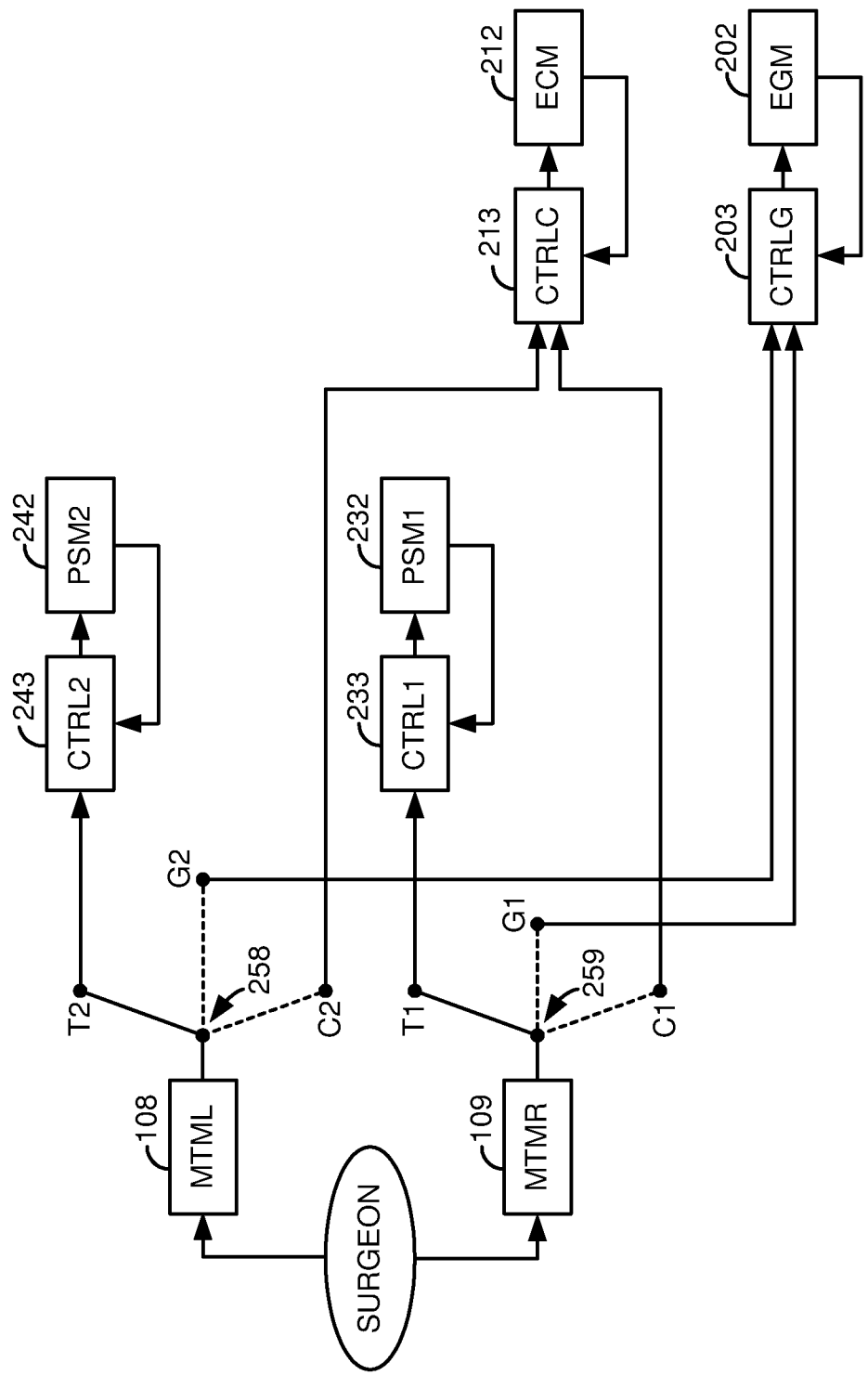
FIG. 2 illustrates a block diagram of components for controlling and selectively associating device manipulators to input devices in a medical robotic system utilizing aspects of the present invention.

FIG. 2 illustrates, as an example, a block diagram of components for controlling and selectively associating device manipulators to the input devices 108, 109. Various surgical tools such as graspers, cutters, and needles may be used to perform a medical procedure at a work site within the Patient. In this example, two surgical tools 231, 241 are used to robotically perform the procedure and the camera 211 is used to view the procedure. The instruments 231, 241, 211 are inserted through passages in the entry guide 200. As described in reference to FIG. 1, the entry guide 200 is inserted into the Patient through entry aperture 150 using the setup portion of the robotic arm assembly 130 and maneuvered by the entry guide manipulator (EGM) 202 of the robotic arm assembly 130 towards the work site where the medical procedure is to be performed.

Each of the devices 231, 241, 211, 200 is manipulated by its own manipulator. In particular, the camera 211 is manipulated by a camera manipulator (ECM) 212, the first surgical tool 231 is manipulated by a first tool manipulator (PSM1) 232, the second surgical tool 241 is manipulated by a second tool manipulator (PSM2) 242, and the entry guide 200 is manipulated by an entry guide manipulator (EGH) 202. So as to not overly encumber the figure, the devices 231, 241, 211, 200 are not shown, only their respective manipulators 232, 242, 212, 202 are shown in the figure.

Each of the instrument manipulators 232, 242, 212 is a mechanical assembly that carries actuators and provides a mechanical, sterile interface to transmit motion to its respective articulatable instrument. Each instrument 231, 241, 211 is a mechanical assembly that receives the motion from its manipulator and, by means of a cable transmission, propagates it to the distal articulations (e.g., joints). Such joints may be prismatic (e.g., linear motion) or rotational (e.g., they pivot about a mechanical axis). Furthermore, the instrument may have internal mechanical constraints (e.g., cables, gearing, cams and belts, etc.) that force multiple joints to move together in a pre-determined fashion. Each set of mechanically constrained joints implements a specific axis of motion, and constraints may be devised to pair rotational joints (e.g., joggle joints). Note also that in this way the instrument may have more joints than the available actuators. In contrast, the entry guide manipulator 202 has a different construction and operation, as will be described below in reference to FIG. 5.

In this example, each of the input devices 108, 109 may be selectively associated with one of the devices 211, 231, 241, 200 so that the associated device may be controlled by the input device through its controller and manipulator. For example, by placing switches 258, 259 in their respective tool following modes "T2" and "T1", the left and right input devices 108, 109 may be respectively associated with the first and second surgical tools 231, 241, which are telerobotically controlled through their respective controllers 233, 243 (preferably implemented in the processor 102) and manipulators 232, 242 so that the Surgeon may perform a medical procedure on the Patient while the entry guide 200 is locked in place.

When the camera 211 or the entry guide 200 is to be repositioned by the Surgeon, either one or both of the left and right input devices 108, 109 may be associated with the camera 211 or entry guide 200 so that the Surgeon may move the camera 211 or entry guide 200 through its respective controller (213 or 203) and manipulator (212 or 202). In this case, the disassociated one(s) of the surgical tools 231, 241 is locked in place relative to the entry guide 200 by its controller. For example, by placing switches 258, 259 respectively in camera positioning modes "C2" and "C1", the left and right input devices 108, 109 may be associated with the camera 211, which is telerobotically controlled through its controller 213 (preferably implemented in the processor 102) and manipulator 212 so that the Surgeon may position the camera 211 while the surgical tools 231, 241 and entry guide 200 are locked in place by their respective controllers 233, 243, 203. If only one input device is to be used for positioning the camera, then only one of the switches 258, 259 is placed in its camera positioning mode while the other one of the switches 258, 259 remains in its tool following mode so that its respective input device may continue to control its associated surgical tool.

On the other hand, by placing switches 258, 259 respectively in entry guide positioning modes "G2" and "G1", the left and right input devices 108, 109 may be associated with the entry guide 200, which is telerobotically controlled through its controller 203 (preferably implemented in the processor 102) and manipulator 202 so that the Surgeon may position the entry guide 200 while the surgical tools 231, 241 and camera 211 are locked in place relative to the entry guide 200 by their respective controllers 233, 243, 213. As with the camera positioning mode, if only one input device is to be used for positioning the entry guide, then only one of the switches 258, 259 is placed in its entry guide positioning mode while the other one of the switches 258, 259 remains in its current mode.

The selective association of the input devices 108, 109 to other devices in this example may be performed by the Surgeon using the GUI 170 or the voice recognition system 160 in a conventional manner. Alternatively, the association of the input devices 108, 109 may be changed by the Surgeon depressing a button on one of the input devices 108, 109 or depressing the foot pedal 105, or using any other well known mode switching technique.

As shown in a perspective view of the entry guide 200 in FIG. 5, the entry guide 200 is generally cylindrical in shape and has a longitudinal axis X' running centrally along its length. The pivot point, which is also referred to as a remote center "RC", serves as an origin for both a fixed reference frame having $x_0$, $y_0$ and $z_0$ axes as shown and an entry guide reference frame having X', $y_0$ and Z' axes as shown. When the system 100 is in the entry guide positioning mode, the entry guide manipulator 202 is capable of pivoting the entry guide 200 in response to movement of one or more associated input devices about the $y_0$ axis (which remains fixed in space) at the remote center "RC" in yaw (OY) In addition, the entry guide manipulator 202 is capable of pivoting the entry guide 200 in response to movement of the one or more input devices about the Z' axis (which is orthogonal to and moves accordingly with the longitudinal axis X' of the entry guide 200) in pitch (OP), capable of rotating the entry guide 200 about its longitudinal axis X' in roll (RO), and linearly moving the entry guide 200 along its longitudinal axis X' in insertion/retraction or in/out "I/O" (or IO) directions in response to movement of the one or more associated input devices. Note that unlike the $y_0$ axis which is fixed in space, the X' and Z' axes move with the entry guide 200. Since the yaw, pitch and roll are respectively performed about the $y_0$, Z' and X' axes, these axes are also referred to herein as the OY, OP and RO axes.

Figure 6:
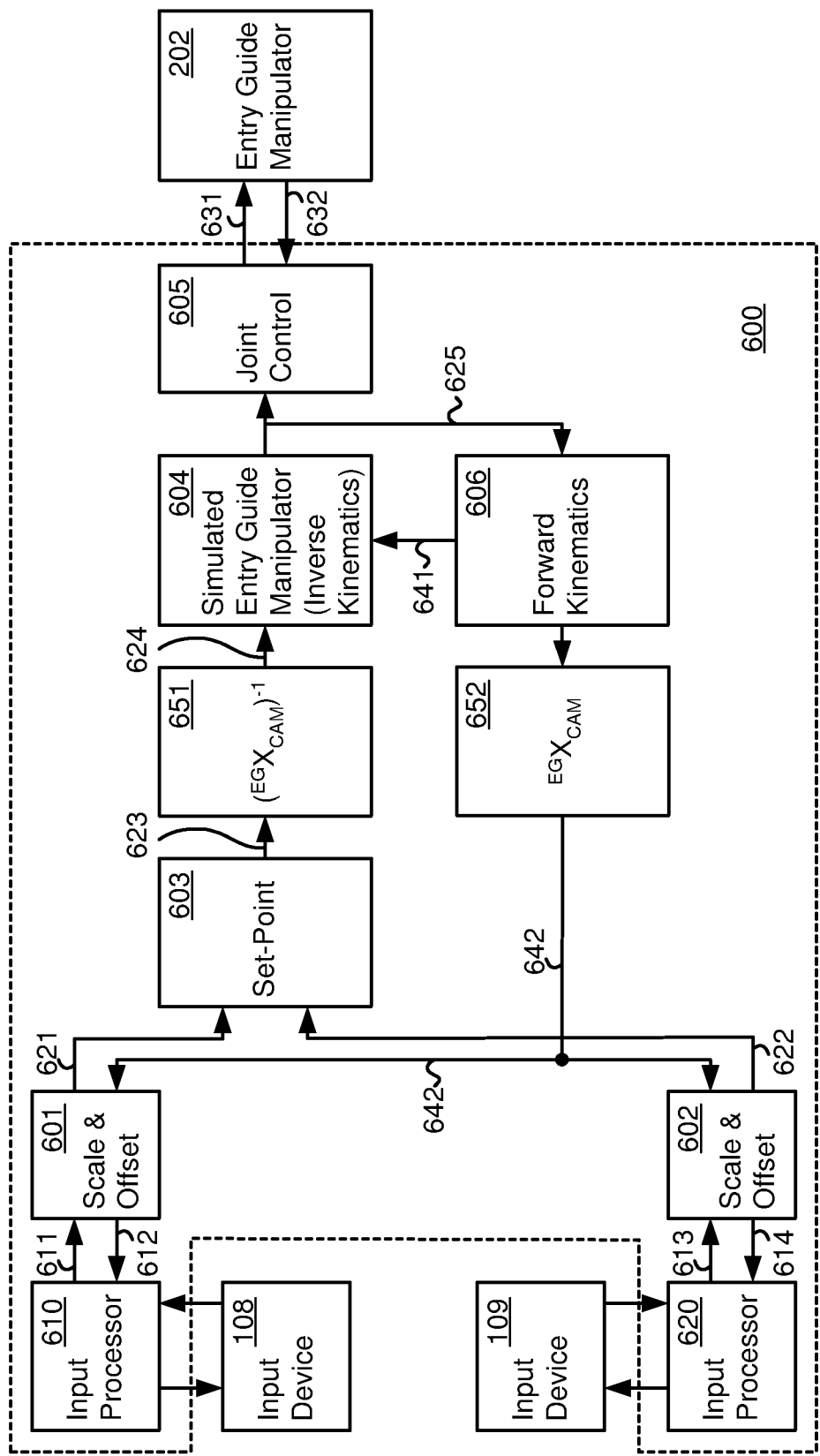
FIG. 6 illustrates a block diagram of an entry guide controller used to control an entry guide manipulator in a medical robotic system utilizing aspects of the present invention.

FIG. 6 illustrates, as an example, a block diagram of a controller 600 (which is one version of the controller 203) for controlling movement of the entry guide 200 in response to movement of the input devices 108, 109 when the input devices 108, 109 are selectively associated with the entry guide 200 in their respective entry guide positioning modes "G2" and "G1". In this example, both input devices 108, 109 are used to move the entry guide 200 according to an image referenced control scheme as the Surgeon views images captured by the camera 211. Alternatively, only one of the input devices 108, 109 may be used, and in lieu of the image referenced control described herein, a tip referenced control scheme such as conventionally used to control individual surgical instruments may be used to move the entry guide 200. In any such alternative, however, the articulatable camera 211, which extends out the distal end of the entry guide 200, is preferably "soft" locked (through its controller 213) at its current position relative to the entry guide 200 during the entry guide positioning mode.

In an image referenced control, the controller 600 controls movement of the entry guide 200 while the Surgeon is given the impression that he or she is moving the image captured by the camera 211. In particular, the Surgeon is provided with the sensation that he or she is grasping the image being displayed on the monitor 104 with his or her left and right hands and moving the image about the work site to a desired viewing point. Note that under this type of control, the image on the monitor 104 appears to move in opposite directions in response to movement of the input devices 108, 109. For example, the image moves to the right when the input devices 108, 109 are moved to the left (and vice versa) and the image moves up when the input devices 108, 109 are moved down (and vice versa).

The input devices 108, 109 include a number of links connected by joints so as to facilitate multiple degrees-of-freedom movement. For example, as the Surgeon moves the input devices 108, 109 from one position to another, sensors associated with the joints of the input devices 108, 109 sense such movement at sampling intervals (appropriate for the processing speed of the controller 102 and entry guide control purposes) and provide digital information indicating such sampled movement in joint space to input processing blocks 610, 620.

Input processing blocks 610, 620 process the information received from the joint sensors of the input devices 108, 109 to transform the information into corresponding desired positions and velocities for the image being displayed on the monitor 104 in a Cartesian space relative to a reference frame associated with the Surgeon's eyes (the "eye reference frame") by computing, for example, joint velocities from the joint position information (or, alternatively, using velocity sensors) and performing the transformation using a Jacobian matrix and eye related information using well-known transformation techniques.

Scale and offset processing blocks 601, 602 receive the processed information 611, 613 from the input processing blocks 610, 620, convert the desired positions and velocities to camera tip positions and velocities in the reference frame of the entry guide 200, and apply scale and offset adjustments to the information so that the resulting movement of the camera 211 and consequently, the image being viewed on the monitor 104 appears natural and as expected by the operator of the input devices 108, 109. The scale adjustment is useful where small movements of the camera 211 are desired relative to larger movement of the input devices 108, 109 in order to allow more precise movement of the camera 211 as it views the work site. To implement the shared control for moving the camera 211 by the input devices 108, 109, lateral offsets are applied to shift the control point to the left for the input device 108 which is being operated by the left hand of the operator and to the right for the input device 109 which is being operated by the right hand of the operator so that each of the input devices 108, 109 appears to control a corresponding view of the stereoscopic image being displayed on the monitor 104. In addition, offset adjustments are applied for aligning the input devices 108, 109 with respect to the Surgeon's eyes as he or she manipulates the input devices 108, 109 to command movement of the camera 211 and consequently, its captured image that is being displayed at the time on the monitor 104.

The outputs 621, 622 of the scale and offset blocks 601, 602 are provided to a set-point generation block 703 so that a single set of position and velocity commands for the camera tip 311 in the reference frame of the entry guide 200 is provided for the entry guide manipulator 202. Therefore, as the operator moves the input devices 108, 109, he or she forces a motion on the mid-point of what feels like to the operator to be a "virtual handlebar". This motion is then "transferred" to subsequent blocks of the controller 600 as a set-point for Cartesian motions.

Figure 8:
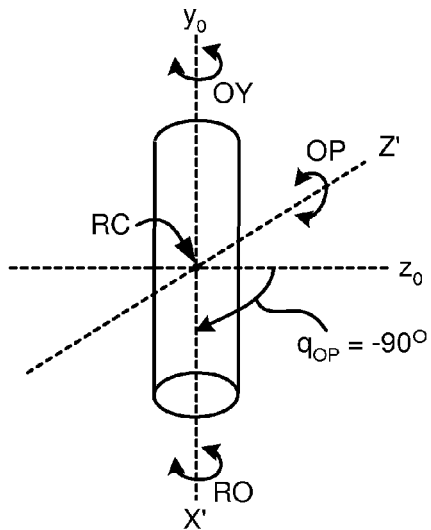
FIG. 8 illustrates a perspective view of an entry guide at a yaw/roll singularity position in a medical robotic system utilizing aspects of the present invention.

Up to this point, the controller 600 has treated the operator movement of the input devices 108, 109 as commanding a corresponding movement of the camera 211 using image referenced control. Ultimately, however, it is the entry guide manipulator 202, not the camera manipulator 213 that is to be moved in response to the operator commands. Therefore, an inverse "entry guide-to-camera" transform $(^{EG}X_{CAM})^{-1}$ block 651 converts the desired movement of the tip of the camera 211 into a desired movement of the tip of the entry guide 202 while still in the reference frame of the entry guide. In particular, as shown in FIG. 8, a camera reference frame <CAM> represents what the Surgeon is seeing at the time on the monitor 104, an entry guide tip reference frame <EG> represents what the controller 600 controls in entry guide positioning mode "G", and a remote center reference frame <REF> represents a fixed reference frame.

A simulated entry guide manipulator block 604 receives the output 624 of the inverse "entry guide-to-camera" transform ($^{EG}X_{CAM}$)$^{-1}$ block 651 and transforms the commanded position and velocity for the distal end of the entry guide 200 from its Cartesian space to corresponding desired joint positions and velocities for the entry guide manipulator (ECM) 202 (e.g., EGM joint space) using the known inverse kinematics of the entry guide manipulator 202 and characteristics of the entry guide 200. In doing so, the simulated entry guide manipulator block 604 manages operation of the entry guide manipulator 202 through singularities and limits its commanded joint positions and velocities to avoid physical or other limitations.

The output 625 of the simulated entry guide manipulator block 604 is then provided to an EGM joint controller block 605 and a forward kinematics block 606. The joint controller block 605 includes a joint control system for each controlled joint (i.e., each mechanical element controlling one of the four degrees-of-freedom described in reference to FIG. 5) of the entry guide manipulator 202, and the output 625 of the simulated entry guide manipulator block 604 provides, as its inputs, the commanded value for each joint of the entry guide manipulator 202. For feedback control purposes, sensors associated with each of the controlled joints of the entry guide manipulator 202 provide sensor data 632 back to the joint controller block 605 indicating the current position and/or velocity of each joint of the entry guide manipulator 202. The sensors may sense this joint information either directly (e.g., from the joint on the entry guide manipulator 202) or indirectly (e.g., from the actuator in the entry guide manipulator 202 driving the joint). Each joint control system in the joint controller 605 then generates torque or other appropriate commands for its respective actuator (e.g., motor) in the entry guide manipulator 202 so as to drive the difference between the commanded and sensed joint values to zero in a conventional feedback control system manner.

The forward kinematics block 606 transforms the output 625 of the simulated entry guide manipulator block 604 from joint space back to the Cartesian space of the entry guide manipulator 202 using the forward kinematics of the entry guide manipulator 202. The output of the forward kinematics block 606 is then translated in an "entry guide-to-camera" transformation ($^{EG}X_{CAM}$) block 652 so that the controller 600 operates once again in camera referenced control mode.

The scale and offset blocks 601, 602 perform an inverse scale and offset functions on the output 642 of the "entry guide-to-camera" transformation ($^{EG}X_{CAM}$) block 652 (as well as performing a reversal of the set-point generation) before passing their respective outputs 612, 614 to the input processing blocks 610, 620 where error values are calculated between their respective outputs 611, 613 and inputs 612, 614. If no limitation or other constraint had been imposed on the input 624 to the simulated entry guide manipulator block 604, then the calculated error values would be zero. On the other hand, if a limitation or constraint had been imposed, then the error value is not zero and it is converted to a torque command that drives actuators in the input devices 108, 109 to provide force feedback felt by the hands of their operator. Thus, the operator becomes aware that a limitation or constraint is being imposed by the force that he or she feels resisting his movement of the input devices 108, 109 in that direction. In addition to this force feedback, forces coming from other sensors or algorithms may be superimposed on the force feedback.

An output 641 of the forward kinematics block 606 may also be provided to the simulated entry guide manipulator block 604 for control purposes. For example, the simulated position output may be fed back and compared with the commanded position.

One singularity that the entry guide manipulator 202 may encounter during its operation is a yaw/roll singularity. As illustrated in FIG. 8, this singularity occurs when the pitch angle $q_{OP}$ of the entry guide 200 is at either +90 degrees or −90 degrees (i.e., in a vertical position) so that the yaw (OY) axis (which is fixed) and roll (RO) axis (which moves with the entry guide 200) coincide. Note that the entry guide manipulator 202 loses the capability of actuating motion of the entry guide 200 in any arbitrary direction in the ($x_0$, $z_0$) plane at this singularity. In particular, only motion perpendicular to the OP axis can be freely actuated in the ($x_0$, $z_0$) plane.

One problem with the yaw/roll singularity is the control ambiguity that it causes. The simulated entry guide manipulator block 604 uses the inverse Jacobian to transform a commanded position and velocity for the distal end of the entry guide 200 from its Cartesian space to the joint space of the entry guide manipulator 202 according to the following equation:

$$\dot{\vec{q}} = J^{-1}(\vec{q}) {}^0\dot{\vec{x}}_{DES} \quad (1)$$

where "$\dot{\vec{q}}$" and "$\vec{q}$" are the joint velocity and position vectors, "$J^{-1}$" is the inverse Jacobian, and "${}^0\dot{\vec{x}}_{DES}$" is the commanded (or desired) state in terms of a Cartesian velocity vector for the distal tip of the entry guide 200 with respect to the remote center reference frame <REF>.

The inverse of the rotation part of the Jacobian may be expressed as follows:

$$\begin{bmatrix} \dot{q}_{OY} \\ \dot{q}_{OP} \\ \dot{q}_{RO} \end{bmatrix} = \begin{bmatrix} -\frac{\sin q_{OY} \sin q_{OP}}{\cos q_{OP}} & -1 & \frac{\cos q_{OY} \sin q_{OP}}{\cos q_{OP}} \\ -\cos q_{OY} & 0 & -\sin q_{OY} \\ \frac{\sin q_{OY}}{\cos q_{OP}} & 0 & -\frac{\cos q_{OY}}{\cos q_{OP}} \end{bmatrix} \begin{bmatrix} {}^0\omega_x \\ {}^0\omega_y \\ {}^0\omega_z \end{bmatrix} \quad (2)$$

Figure 10:
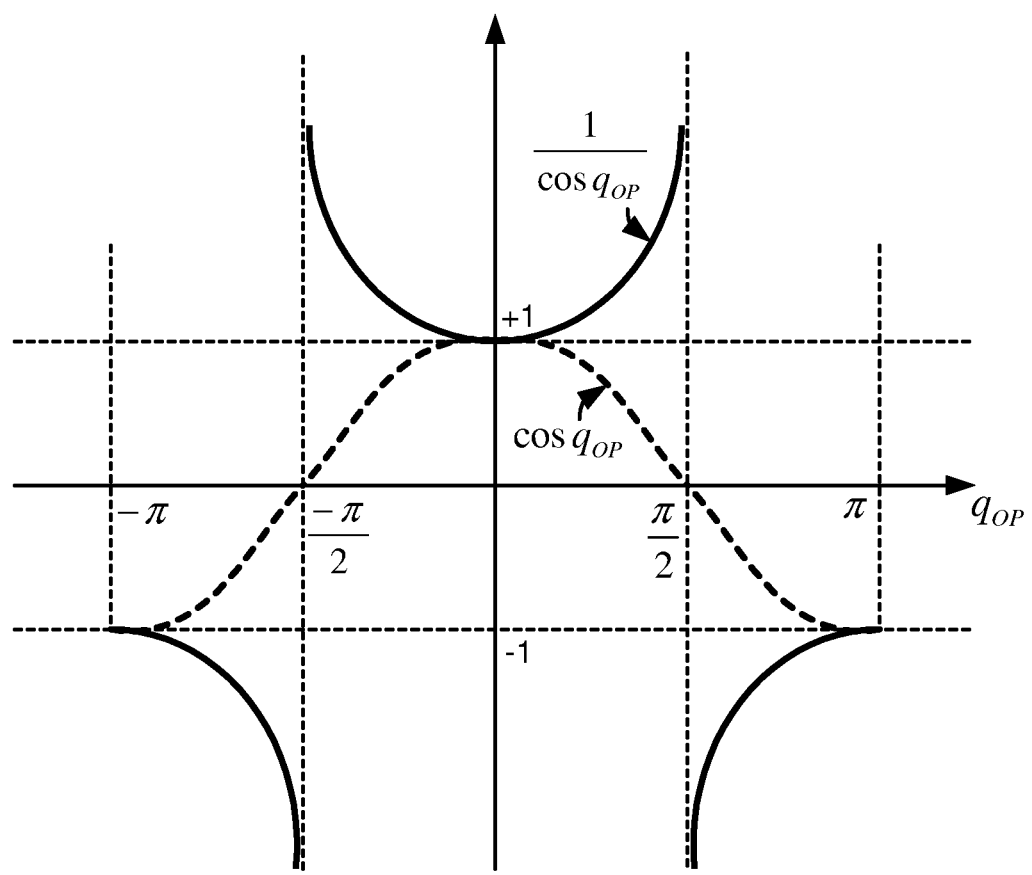
FIG. 10 illustrates a plot of 1/cos $q_{OP}$ vs. $q_{OP}$ as an entry guide approaches a yaw/roll singularity in a prior art medical robotic system.

As the entry guide pitch angle $q_{OP}$ approaches the entry guide manipulator's yaw-roll singularity, the term "cos $q_{OP}$" approaches zero and the term "1/cos $q_{OP}$" approaches infinity as shown in FIG. 10, and as a consequence, the roll and yaw joint velocities, $\dot{q}_{RO}$ and $\dot{q}_{OY}$, become very large until they become saturated by programmed limits in the simulated entry guide manipulator block 604. Stated differently, the $\dot{q}_{RO}$ and $\dot{q}_{OY}$ joint velocities tend to become very large because there is no unique solution to the following equation:

$$ {}^0\omega_{y,DES} = -\dot{q}_{OY} + \dot{q}_{RO} \quad (3)$$

Any combination of ($\dot{q}_{RO}$, $\dot{q}_{OY}$) such that their difference corresponds to the desired angular velocity about the fixed OY axis satisfies the inverse kinematics, but the individual $\dot{q}_{RO}$ and $\dot{q}_{OY}$ joint velocities can be very large.

Figure 9:
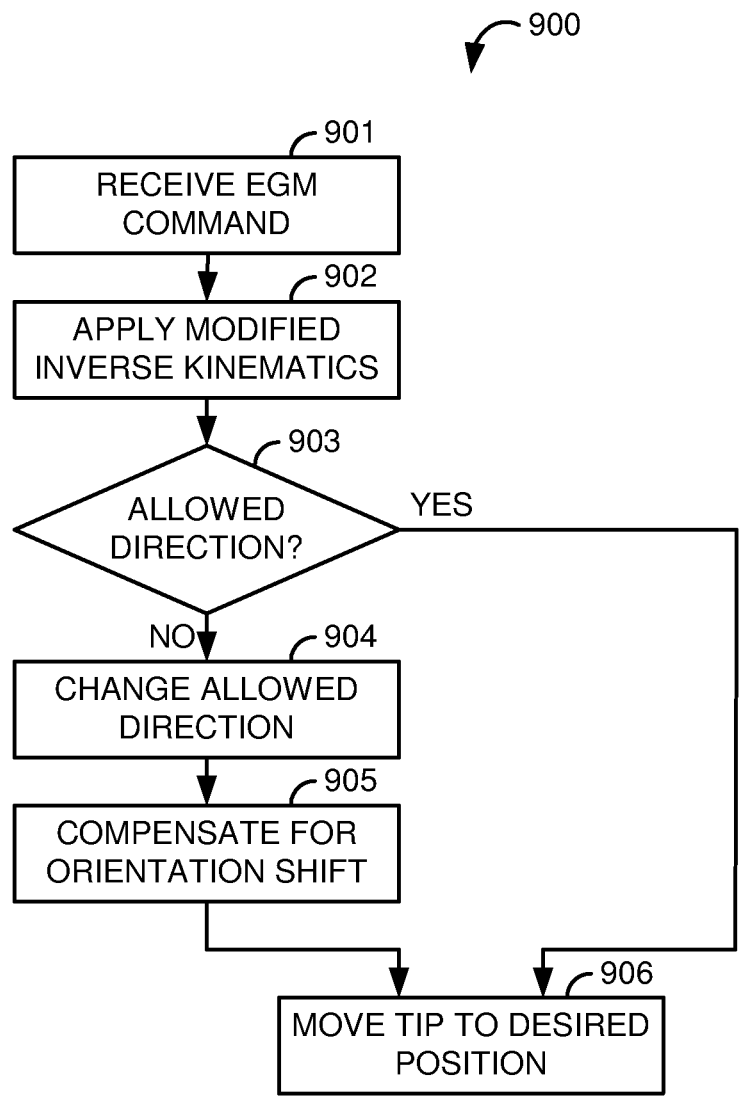
FIG. 9 illustrates a flow diagram of a method for controlling an entry guide manipulator near a singularity in a medical robotic system utilizing aspects of the present invention.

FIG. 9 illustrates, as an example, a flow diagram of a method 900 which is implemented in the entry guide manipulator controller 203 for commanding the entry guide manipulator 202 to manipulate the entry guide 200. In 901, an entry guide manipulator command, which indicates a commanded state (e.g., position and orientation) of the entry guide 200, is received from at least one of the input devices 108, 109. In 902-905, the method then resolves any control ambiguity caused by a yaw/roll singularity. Although shown as sequential tasks in a particular order, the tasks performed in 902-905 may be concurrently and/or in any order.

Figure 11:
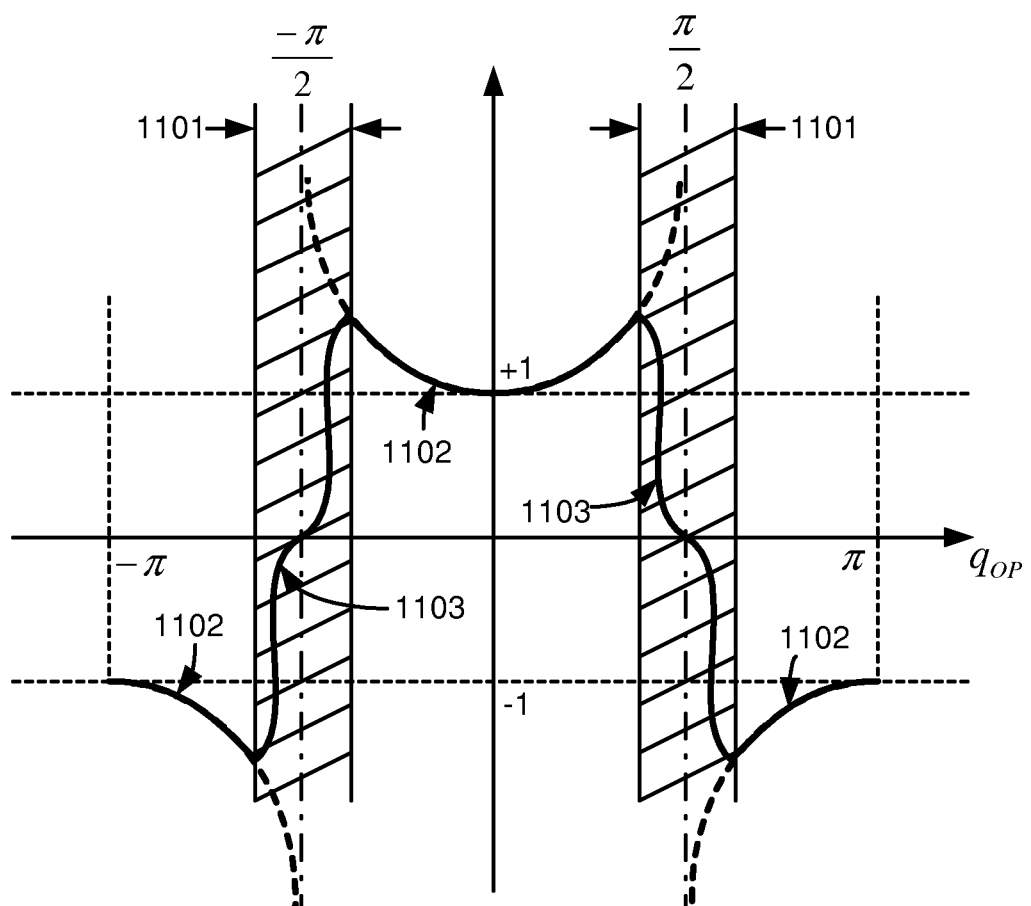
FIG. 11 illustrates a plot of 1/cos $q_{OP}$ vs. $q_{OP}$ as an entry guide approaches a yaw/roll singularity in a medical robotic system utilizing aspects of the present invention.

In 902, the method applies modified inverse kinematics to the commanded state to determine joint state commands for driving joint actuators in the entry guide manipulator 203 in a smooth and controllable manner. As an example of such application of modified inverse kinematics, a modified inverse Jacobian is applied in the simulated entry guide manipulator block 604 by modifying the previously described inverse Jacobian to avoid commanding excessive $\dot{q}_{RO}$ and $\dot{q}_{OY}$ joint velocities near and at the singularity, wherein the term "1/cos $q_{OP}$" is replaced with the following function "$\gamma(q_{OP})$" in equation (2):

$$\gamma(q_{OP}) = \begin{cases} \text{function 1102 for } q_{OP} \text{ outside 1101} \\ \text{function 1103 for } q_{OP} \text{ inside} \\ \text{and at the limits of 1101} \end{cases} \quad (4)$$

where, as shown in FIG. 11, the threshold distance as indicated by the range 1101 is preferably ±0.3 radians about −Π/2 radians and ±0.3 radians about Π/2 radians (to avoid commanding the high joint velocities); the function 1102 is "1/cos $q_{OP}$"; and the function 1103 is a preferably smooth function that is zero at the singularity (i.e., −Π/2 radians and Π/2 radians).

Equation (2) is thus modified as follows to define a modified version of the inverse Jacobian:

$$\dot{q}_{OP} = -\cos q_{OY}{}^0\omega_x - \sin q_{OY}{}^0\omega_z \quad (5)$$

$$\dot{q}_{RO} = \gamma(q_{OP})[\sin q_{OY}{}^0\omega_x - \cos q_{OY}{}^0\omega_z] \quad (6)$$

$$\dot{q}_{OY} = -\sin q_{OP}\gamma(q_{OP})[\sin q_{OY}{}^0\omega_x - \cos q_{OY}{}^0\omega_z] - {}^0\omega_y \quad (7)$$

By implementing equations (5)-(7) in the simulated entry guide manipulator block 604, the roll joint velocity $\dot{q}_{RO}$ approaches zero and the yaw joint velocity $\dot{q}_{OY}$ actuates the commanded ${}^0\omega_y$ from the operator of the input devices 108, 109 as the entry guide 200 approaches the yaw/roll singularity of the entry guide manipulator 202. Thus, the excessive joint velocity problem caused by the entry guide manipulator's yaw and roll axes coinciding at the singularity is avoided.

It is to be appreciated that other techniques, such as dynamic low pass filtering, which are position dependent and result in smooth behavior may be used instead of the "$\gamma(q_{OP})$" function in 902, to compute an appropriate modified inverse Jacobian when the manipulator is close to the singularity, while leaving it essentially unchanged away from the singularity.

In 903, the method determines whether the commanded state of the entry guide 200 is in an allowed direction, which is the direction in which force feedback on the input devices 108, 109 is such that entry guide motion along a plane including the RO and OY axes has little to no resistance while motion away from that plane is more heavily resisted. Stated in another way, the "allowed direction" is one in which a point in space may be reached using only a pitch rotation about the OP axis and I/O translation as necessary along the RO axis. Conversely, a "forbidden direction" is any direction parallel to the OP axis and perpendicular to the "allowed direction". It is to be appreciated that a generic desired Cartesian velocity vector $\dot{X}_{des}$ can always be split into its components along the "allowed direction" and along the "forbidden direction".

It can be shown that the allowed direction "${}^0\hat{1}$" in the ($x_0, z_0$) plane is represented by the unit vector:

$$^0\hat{1} = \begin{bmatrix} \sin q_{OY} \\ 0 \\ -\cos q_{OY} \end{bmatrix} \quad (8)$$

If the determination in 903 is YES, i.e., the commanded state is in the allowed direction, then in 906, the entry guide controller 203 commands the entry guide manipulator 202 to move the entry guide 200 to the commanded state by using only a pitch rotation about the OP axis and I/O translation as necessary along the RO axis.

On the other hand, if the determination in 903 is NO, i.e., the commanded state is not in the allowed direction, then in 904, the entry guide controller 203 commands the entry guide manipulator 202 to manipulate the entry guide 200 so as to change the allowed direction to one where the commanded state may be reached with little to no resistance to the operator on the input devices 108, 109. As indicated in equation (8), since the allowed direction only depends on the yaw joint angle $q_{OY}$, the allowed direction may be relocated in space simply by commanding rotation of the yaw joint of the entry guide manipulator 202.

Figure 13:
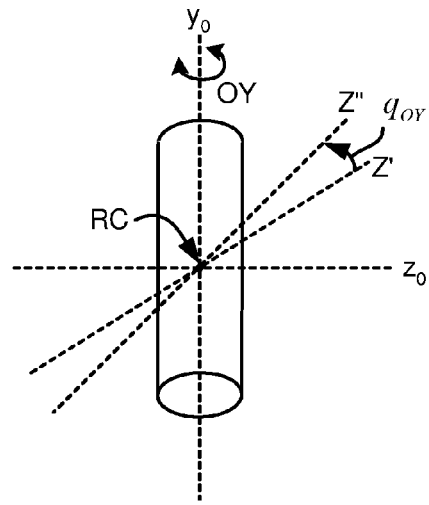
FIG. 13 illustrates a perspective view of an entry guide as its allowed direction is changed at a yaw/roll singularity in a medical robotic system utilizing aspects of the present invention.
Figure 12:
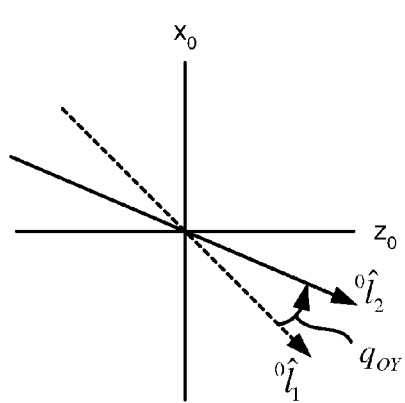
FIG. 12 illustrates an $x_0$-$z_0$ plane view as an allowed direction of the entry guide is changed at a yaw/roll singularity in a medical robotic system utilizing aspects of the present invention.

A graphical representation of repositioning the allowed direction is shown in FIG. 12, wherein the allowed direction may be repositioned from ${}^0\hat{1}_1$ to ${}^0\hat{1}_2$ by rotating the yaw joint $q_{OR}$, and a corresponding perspective view of the entry guide is shown in FIG. 13, wherein the pitch axis has moved from Z' to Z'' by rotating the yaw joint $q_{OY}$.

By rotating the entry guide 200 about its yaw axis to change the allowed direction, each of the articulated instruments 211, 231, 241 extending out of its distal end also rotates at the yaw/roll singularity about the central longitudinal axis X' of the entry guide 200 accordingly. However, if the operator of the input devices 108, 109 does not intend such a rotation, then it is necessary to rotate the instruments back to their original positions without using a yaw rotation $q_{OY}$ so that the allowed direction remains where it has been repositioned. This is especially important for maintaining the orientation of images captured by the camera 211 that are being displayed at the time on the display screen of the monitor 104.

In 905, the roll rotational degree of freedom of the entry guide manipulator 202 is used to provide the necessary compensating rotation after or concurrently with 904. As an example, FIGS. 15-17 illustrate sequential views of an entry guide tip as its allowed direction 1502 is repositioned and its orientation realigned at the yaw/roll singularity. In FIG. 15, the desired direction (as indicated by the velocity vector $\dot{X}_{des}$) of the entry guide tip is in a different direction than the current allowable direction "${}^0\hat{1}$" 1502 of the entry guide 200. So, as shown in FIG. 16, the yaw joint of the entry guide manipulator 202 is actuated (as indicated by its velocity $\dot{q}_{OY}$) to rotate the entry guide tip 1501 (and the allowable direction 1502) so as to include the desired direction $\dot{X}_{des}$. Finally, as shown in FIG. 17, the roll joint of the entry guide manipulator 202 is actuated (as indicated by the velocity $\dot{q}_{RO}$) to compensate for the orientation change caused by the yaw movement.

In the process described in reference to FIGS. 15-17, the operator of the input devices 108, 109 perceives through force feedback a vanishing resistance in the direction of the motion on the input devices 108, 109, which represents the finite velocity with which the entry guide manipulator 202 of the robotic arm 130 is repositioning its joints to accommodate the command. As a consequence, only "slow" motions are generally performable using the control strategy described herein.

Note that since the entry guide manipulator's yaw and roll joints have finite ranges of motion, one of the two joints might hit a limit before the other, thus "destroying" the illusion created by the described orientation control scheme. To prevent this, the simulated entry guide controller 203 preferably saturates the movements of the yaw and roll joints in a "coupled" manner so that if one is limited, the other is limited too.

Also, note that although the roll joint is used for orientation compensation in 905, its use is still disengaged from user control according to 902 when the entry guide 200 is at the yaw/roll singularity. Therefore, if the user desires to rotate the entry guide tip at the yaw/roll singularity, the yaw joint must be used instead. FIGS. 18-19 illustrate, as an example, sequential views of the entry guide tip 1501 during such a pure rotation of the tip about the entry guide's yaw axis at the yaw/roll singularity.

Figure 14:
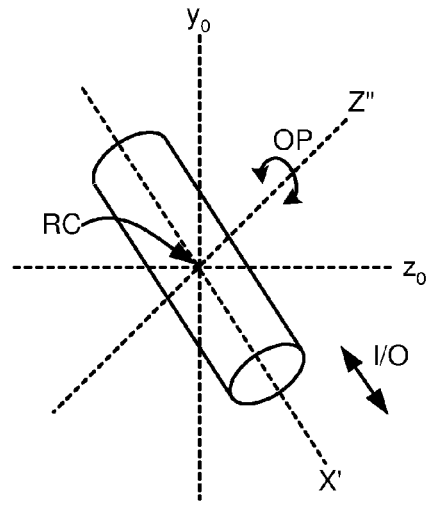
FIG. 14 illustrates a perspective view of an entry guide as it moves to a commanded state in its allowed direction in a medical robotic system utilizing aspects of the present invention.

After changing the allowed direction and compensating for the orientation shift, in 906, the entry guide controller 203 commands the entry guide manipulator 202 to move the entry guide 200 to the commanded state by using only a pitch rotation about the OP axis and I/O translation as necessary along the RO axis, such as shown for example in FIG. 14 which follows the repositioning of the allowed direction in FIG. 13.

Although the various aspects of the present invention have been described with respect to a preferred embodiment, it will be understood that the invention is entitled to full protection within the full scope of the appended claims. For example, although the method is described in reference to a yaw/roll singularity of the entry guide manipulator 203, it is to be appreciated that the general teaching of the method described in reference to FIG. 11 may be generally applied to the control of medical robotic system manipulators about their kinematic singularities.

What is claimed is:

1. A medical robotic system comprising:
   a medical device;
   a manipulator for manipulating the medical device in at least first, second, and third rotational degrees of freedom in which the medical device is respectively rotatable about first, second, and third axes at a pivot point; and
   a controller configured to resolve a control ambiguity caused by the first and third axes coinciding while commanding the manipulator to manipulate the medical device to a commanded state, wherein the controller resolves the control ambiguity by determining whether the commanded state is within an allowed direction defined by a plane of rotation of the second rotational degree of freedom of the manipulator, commanding the manipulator to manipulate the medical device to the commanded state if the commanded state is determined to be in the allowed direction by using the second rotational degree of freedom of the manipulator, and commanding the manipulator to manipulate the medical device to the commanded state if the commanded state is determined not to be in the allowed direction by first changing the allowed direction using the first rotational degree of freedom so that the commanded state is within the allowed direction and then using the second rotational degree of freedom of the manipulator.

2. The medical robotic system according to claim 1, wherein the controller is configured to employ the third degree of freedom of the manipulator for a compensating purpose as the manipulator manipulates the medical device to the commanded state.

3. The medical robotic system according to claim 2, wherein the compensating purpose is to maintain an orientation of an image captured by a camera extending out of a distal end of the medical device.

4. The medical robotic system according to claim 1, wherein the controller is configured to calculate a modified version of inverse kinematics for generating commands for joints of the manipulator to manipulate the medical device to the commanded state so as to avoid commanding joint velocities beyond limitations of the joints.

5. The medical robotic system according to claim 4, wherein the modified version of the inverse kinematics is an inverse Jacobian modified with a function applied to the commanded joint velocities which results in zeroing the commanded joint velocity in the third rotational degree of freedom when the first and third axes coincide.

6. The medical robotic system according to claim 1, wherein the controller is configured to limit the angular velocity of one of the first and third rotational degrees of freedom of the manipulator to its respective limitation value when the angular velocity of the other of the first and third rotational degrees of freedom of the manipulator is limited to its respective limitation value.

* * * * *